(12) United States Patent
Kamiya et al.

(10) Patent No.: US 11,279,911 B2
(45) Date of Patent: Mar. 22, 2022

(54) CELL CULTURE CONTAINER, AUTOMATIC CELL CULTURE APPARATUS, LIQUID CONTAINER, ROBOT HAND, AND ROBOT SYSTEM

(71) Applicants: DENSO WAVE INCORPORATED, Aichi-pref. (JP); ANIMAL STEM CELL, Tokyo (JP)

(72) Inventors: Koji Kamiya, Chita-gun (JP); Wataru Saito, Chita-gun (JP); Kazuhiro Nagaike, Tokyo (JP)

(73) Assignees: DENSO WAVE INCORPORATED, Aichi-Pref. (JP); ANIMAL STEM CELL, Tokyo (JP)

( * ) Notice: Subject to any disclaimer, the term of this patent is extended or adjusted under 35 U.S.C. 154(b) by 714 days.

(21) Appl. No.: 15/634,203

(22) Filed: Jun. 27, 2017

(65) Prior Publication Data
US 2017/0369833 A1   Dec. 28, 2017

(30) Foreign Application Priority Data
Jun. 28, 2016   (JP) .............................. JP2016-127618

(51) Int. Cl.
| C12M 1/36 | (2006.01) |
| B25J 21/00 | (2006.01) |
| B25J 15/08 | (2006.01) |
| B25J 15/00 | (2006.01) |
| B25J 19/02 | (2006.01) |
| C12M 1/24 | (2006.01) |
| C12M 1/00 | (2006.01) |
| C12M 3/00 | (2006.01) |

(52) U.S. Cl.
CPC .......... *C12M 41/48* (2013.01); *B25J 15/0028* (2013.01); *B25J 15/08* (2013.01); *B25J 19/023* (2013.01); *B25J 21/00* (2013.01); *C12M 23/08* (2013.01); *C12M 23/38* (2013.01); *C12M 23/46* (2013.01); *C12M 23/50* (2013.01)

(58) Field of Classification Search
CPC ....... C12M 23/08; C12M 23/38; C12M 41/48
See application file for complete search history.

(56) References Cited

U.S. PATENT DOCUMENTS

| 2007/0026516 A1 | 2/2007 | Martin et al. |
| 2010/0227405 A1 | 9/2010 | Martin et al. |
| 2012/0315693 A1 | 12/2012 | Martin et al. |
| 2013/0260454 A1 | 10/2013 | Martin et al. |
| 2014/0065709 A1 | 3/2014 | Martin et al. |
| 2014/0106386 A1* | 4/2014 | Umeno .............. G01N 35/0099 435/23 |

(Continued)

FOREIGN PATENT DOCUMENTS

| JP | 2002-019884 A | 1/2002 |
| JP | 2002-104476 A | 4/2002 |

(Continued)

*Primary Examiner* — William H. Beisner
(74) *Attorney, Agent, or Firm* — Oliff PLC

(57) ABSTRACT

A bottle includes a body, a cap mounted to a cap neck of the body. The cap has an outer peripheral portion which is provided with a protrusion. Around the cap, there is provided a position indicator indicating whether the cap is at a correctly closed position, based on the positional relationship between the protrusion and the position indicator.

8 Claims, 17 Drawing Sheets

(56) References Cited

U.S. PATENT DOCUMENTS

| | | |
|---|---|---|
| 2014/0106444 A1 | 4/2014 | Martin et al. |
| 2014/0227775 A1 | 8/2014 | Martin et al. |
| 2015/0166208 A1 | 6/2015 | Miyauchi |
| 2015/0232796 A1 | 8/2015 | Martin et al. |
| 2015/0329813 A1 | 11/2015 | Martin et al. |
| 2015/0337252 A1 | 11/2015 | Martin et al. |
| 2017/0029756 A1 | 2/2017 | Nagaike et al. |
| 2017/0058242 A1 | 3/2017 | Martin et al. |

FOREIGN PATENT DOCUMENTS

| | | |
|---|---|---|
| JP | 2003-276712 A | 10/2003 |
| JP | 4550101 B2 | 9/2010 |
| JP | 2015-112704 A | 6/2015 |
| JP | 2015-202894 A | 11/2015 |
| JP | 2016-064112 A | 4/2016 |
| WO | 2015-156367 A1 | 10/2015 |

\* cited by examiner

CELL CULTURE CONTAINER, AUTOMATIC CELL CULTURE APPARATUS, LIQUID CONTAINER, ROBOT HAND, AND ROBOT SYSTEM

CROSS-REFERENCE TO RELATED APPLICATION

This application is based on and claims the benefit of priority from earlier Japanese Patent Application No. 2016-127618 filed Jun. 28, 2016, the description of which is incorporated herein by reference.

BACKGROUND OF THE INVENTION

Technical Field of the Invention

The present invention relates to a cell culture container, an automatic cell culture apparatus, a liquid container, a robot hand handling the container, and a robot system provided with the robot hand.

Related Art

In recent years, robots are being applied to worksites which are associated with medications or medical services. With this trend, isolators used for cell culture tasks and the like have been put into the market. Such an isolator includes a work area where a robot arm is placed so that an operator can externally give commands to the robot arm for cell culture tasks and the like. For example, a patent literature JP 4550101 B discloses a configuration in which materials to be consumed are delivered in and out to/from an automatic cell culture apparatus including an operation robot 19, via a storage and retrieval section 15. In this type of isolator, a robot arm is utilized to improve work efficiency of supplying materials to be consumed and the like handled by the robot arm. In this case, however, maintaining a sterilized state remains as an issue to be addressed.

For example, various kinds of cells isolated from living organisms are cultivated under an artificially simulated living body environment, and genes are transferred into the cells as necessary, to obtain abundant cells and various kinds of factors produced from the cells for use in medical treatment of various diseases. When these tasks are performed by a robot arm, a cell culture medium is assumed to be accommodated in a flask- or bottle-shaped container, with its opening portion being closed by a screw cap, for supply into the work area of the isolator. In this case, the tasks performed by the robot arm in the isolator involve placing the container at a predetermined work position, and grasping and rotating the cap with the end effector to open the cap, and then grasping the container body to transfer the culture medium inside the container to another container, such as a cultivation flask, bottle or laboratory dish.

Most of the culture containers used for automatic cell culture apparatuses for regenerative medicine are generally-used cell-cultivation containers. Such a generally-used cell-cultivation container has an upper portion in which a manufacturer name is indicated or an arrowed opening position is marked at the time of molding the cap; however, the textual information or the arrowed mark tends to be unclear. It is difficult to obtain containers having caps whose shape is suitable for use in automatic cell culture apparatuses or having a clearly indicated mark.

The motions taken by the automatic cell culture apparatus are something previously designed and mechanically controlled. When the series of motions for handling a culture container as mentioned above are iterated, reproducibility is quite high in the positional relationship between the cap and the container body. However, when grasping a cap, if the claws of the robot slide over the cap, an error may occur in the rotational position of the cap, disabling visual recognition of the screw position inside the cap. To cope with this, the positional relationship between the cap and the container body is identified such as by a camera or a sensor when opening/closing the cap. However, the accuracy of this identification is quite low. In fact, there are factors of increasing wear of the cap, such as use of a clutch when the cap is closed, excessive rotation of the cap when opened, or tasks of opening/closing the cap that disturb the directivity of the cap.

When the cap is started to be opened from a closed state, large torque is instantaneously required. This large torque, that is, a grip force of the claws, or rotation torque associated with the robot hand, imposes a large load to the robot hand.

SUMMARY OF THE INVENTION

Assuming that the type of task is as described above, the following issues to be addressed may arise.

(1) The container accommodating a culture medium, which should be in a sterilized state as a precondition, is needed to be supplied into the work area of the isolator without admixture of various bacteria from outside. After the culture medium is supplied, but before the robot arm starts the task of opening the container in the work area, it is necessary to confirm that the cap of the container is reliably fastened and the container is completely closed to prevent contamination of the work area due to the admixture of various germs or the like.

For example, if the cultivated cells are contaminated by another person's cells, the cultivated cells are no longer usable. Therefore, the cells or the solution in the bottle need to be prevented from leaking out into the work environment inside the isolator. To this end, it is necessary to confirm that the container is completely closed by the cap. The example taken herein deals with the tasks performed under a sterilized environment. However, aside from these tasks, confirming reliable fastening of a cap is necessary, in general, to prevent leakage of a solution or the like accommodated in the container.

(2) Considering ease of manufacture or cost reduction, the material used for the bottle-shaped container is assumed to be a resin, such as polyethylene terephthalate or polystyrene. A robot hand, on the other hand, is usually formed of metal having high rigidity, which is different from a human hand. Accordingly, when a robot hand grasps and rotates the cap of a container, with the container body being fixed, if the grasped state is incomplete and friction is caused between the robot hand and the cap, the surface of the cap made of resin may be abraded by the robot hand to thereby produce wear debris. Production of such wear debris, which leads to contamination inside the working chamber, is needed to be prevented. The structure of the cap can cause positional displacement when the robot hand opens and closes the cap in two opposite direction.

The present disclosure has been made in light of the circumstances set forth above and has an object to provide a liquid container facilitating the opening task performed by a robot hand, a robot hand having a configuration suitable for the opening task for the liquid container, and a robot system including the robot hand, and to provide a cell culture container facilitating confirmation on the closed state of the container, and an automatic cell culture apparatus using the container.

According to an aspect of the present disclosure, a cell culture container includes a container body accommodating a cell culture medium; a cap mounted to an opening portion of the container body; and a mark used for confirming correctness as to a closed state of the cap. In the cell culture container, provision of the mark enables easy confirmation on the correctness of the closed state of the cap which is mounted to the opening portion of the container body accommodating a cell culture medium.

The cell culture container of the present disclosure may include a torque receiver provided to the cap, and a reference mark provided to the container body. In the cell culture container, provision of the torque receiver and the reference mark enables confirmation on the closed state of the cap, based on the positional relationship between them.

The cell culture container of the present disclosure may include a protrusion provided to an outer peripheral surface of the cap. The protrusion can receive torque applied to the cap during an opening task performed on the cell culture container.

According to the cell culture container of the present disclosure the protrusion may have a length of 1 mm or more.

According to the cell culture container of the present disclosure provided with the protrusion, the protrusion reduces displacement during an opening task or a closing task, or reduces load during an opening task. Specifically, provision of the protrusion enables confirmation, in terms of the appearance, on the starting and ending positions of the thread ridge or the thread groove formed on the inside of the cap. More specifically, since both the starting and ending positions of the thread at the opening portion of the container body can be confirmed from the appearance, the container can be opened or closed with only a motion associated with the thread pitch. Further, the container body can be firmly fixed via planar cell observation surfaces of the container body and each having a comparatively large area, and, if handled by a robot hand, for example, the shapes of the cap and protrusion can be designed taking account of a combination with the shape of the robot hand, to thereby facilitate transmission of torque during the opening or closing task.

According to the cell culture container of the present disclosure provided with the protrusion, the protrusion may have a tip end which is located at a position radially inside an outer periphery of the container body, as viewed from above the cap in a closed state. With this configuration, when handling the cell culture container, the protrusion of the cap does not hinder the tasks. Further, when the cell culture container is handled by a robot hand, for example, the grip force at the claw of the hand can be reduced. Furthermore, since the motion radius becomes large, a comparatively large torque can be applied to the cap, because the motion radius influences linearly a torque applied during an opening/closing task.

According to an aspect of the present disclosure, an automatic cell culture apparatus handles the above-mentioned cell culture container. The automatic cell culture apparatus includes an imager which outputs data of a captured image and a control apparatus which acquires image data of the mark imaged by the imager to determine whether the cap is in a correctly closed state. Specifically, by confirming the position of the mark of the cell culture container in the image, the control apparatus can determine whether the cap is in a correctly closed state.

The automatic cell culture apparatus handling the cell culture container that is provided with the protrusion, includes the imager, the control apparatus and a robot hand which performs an opening task for the cell culture container. The robot hand performs an opening task for the cell culture container by applying torque in the range of 0.7 Nm or more and 1.5 Nm or less to the torque receiver of the cap. Accordingly, the cap is rotated and opened with only a comparatively small torque being applied to the cap.

According to the automatic cell culture apparatus of the present disclosure provided with the robot hand, the robot hand is provided to the arm of a small robot. The arm of a small robot can be arranged in a working chamber of the automatic cell culture apparatus where a sufficiently large space is difficult to find to perform the opening task for the cell culture container.

According to an aspect of the present disclosure, a liquid container has a configuration including a container-shaped, e.g. a bottle-shaped, body and a cap mounted to an opening portion of the container-shaped body. In the configuration, a protrusion is provided to an outer peripheral portion of the cap. Further, the area around the opening portion is provided with a position indicator indicating whether the cap is at a correctly closed position on the basis of the positional relationship between the protrusion and the position indicator.

With this configuration, the robot can acquire information on the positional relationship between the protrusion of the cap and the position indicator, prior to performing the opening task, from an image captured by a camera or the like arranged at the robot hand, to thereby determine whether the cap is at a correctly closed position. Further, the opening task with the robot hand grasping the cap can be started, for example, with the claw of the hand abutting against the protrusion. Thus, when the robot hand is rotated, friction does not occur between the cap and the robot hand to thereby prevent production of wear debris.

Further, the robot can acquire information on the amount of rotation of the cap from an initially closed state, from the positional relationship between the protrusion and the position indicator. Accordingly, information on the amount of rotation required for opening the cap can also be obtained, and thus the opening task is facilitated.

According to the liquid container of the present disclosure, the position indicator may include a plurality of small areas that can be discriminated from each other, the small areas being obtained by dividing an area around the opening portion in a circumferential direction. With this configuration, the positional relationship between the cap and the body can be more easily and more specifically confirmed.

According to the liquid container of the present disclosure, the protrusion may have a tip end which is located at a position radially inside an outer periphery of the container-shaped body, as viewed from above the cap in a closed state. With this configuration, the protrusion provided to the cap does not hinder tasks performed when the cell culture container is handled.

According to an aspect of the present disclosure, a robot hand performs an opening task for the liquid container. The robot hand includes two or more claws, and an imager. The imager captures an image of the position indicator of the liquid container body and identifies the image of the position indicator captured by the imager. Thus, the robot can acquire information on the positional relationship between the cap and the body, to thereby perform the opening task by grasping the cap with the two or more claws.

The robot hand of the present disclosure may include a recess to be engaged with the protrusion, the recess being provided to a tip end of at least one claw. Thus, the cap can be easily rotated with the claw being engaged with the protrusion. With this configuration, friction does not occur between the cap and the claw, to thereby more reliably prevent production of wear debris.

The robot hand of the present disclosure may include two claws. Since the robot hand has only two claws, only a minimum number of openings is required to be provided for establishing communication between the exterior and the interior in which the actuators for driving the claws are provided, leading to easy sealing of the openings. Accordingly, a structure adapted for improving cleaning properties can be provided.

The robot hand of the present disclosure provided with the recess may include two or more claws provided with respective recesses. With this configuration, the claws can be more easily engaged with the protrusion of the cap.

According to an aspect of the present disclosure, a robot system includes a robot arm having the above-mentioned robot hand; and a control apparatus controlling the robot arm. The control apparatus acquires data of an image which has been captured by the imager provided to the robot hand, the image including the cap and the position indicator of the liquid container, and determines whether the cap is at a correctly closed position, based on a positional relationship between the protrusion of the cap and the position indicator. Thus, non-contamination of the material or the like accommodated in the liquid container can be confirmed prior to performing an opening task for the liquid container.

According to the robot system of the present disclosure, when the cap is determined to be at a correctly closed position, the control apparatus may cause the robot hand to grasp and rotate the cap in an opening direction by a predetermined angle to perform an opening task for the liquid container. With this configuration, while confirming the positional relationship between the protrusion of the cap and the position indicator from the image data, the opening task can be reliably performed.

According to the robot system of the present disclosure, when the cap is determined not to be at a correctly closed position, the control apparatus may cause the robot hand to grasp and rotate the cap in a closing direction by a predetermined angle to perform a closing task for the liquid container, and the may cause the robot hand to discard the closed liquid container. Specifically, if the liquid container has not been properly closed, the material or the like accommodated in the container may have been contaminated. Therefore, the liquid container is discarded after being completely closed so that the material or the like accommodated therein does not leak out, thereby preventing contamination inside the working chamber where the robot arm performs tasks.

DETAILED DESCRIPTION OF THE PREFERRED EMBODIMENTS

First Embodiment

Figure 1A:
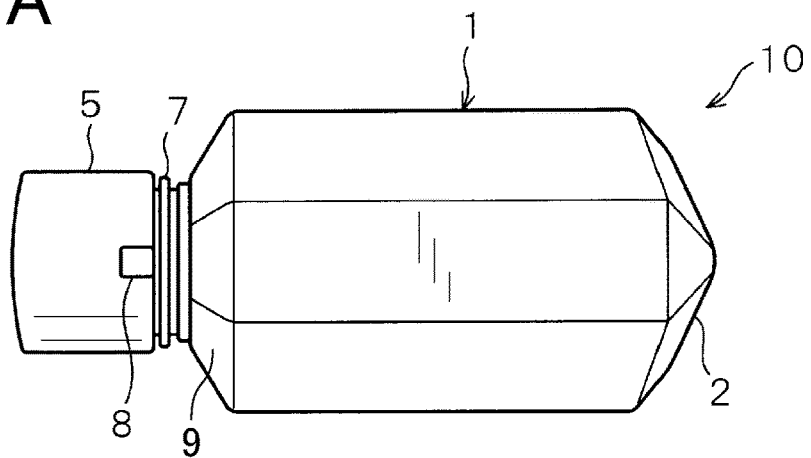
FIGS. 1A and 1B are side view and plan view, respectively, of a bottle serving as a cell culture container, according to a first embodiment of the present invention.

The following description addresses a first embodiment of the present invention. As shown in FIGS. 1A and 1B, and FIGS. 2 to 4, a bottle 10 serving as a cell culture container of the present embodiment has a body 1 in an octagonal prism shape including a closed lower end part 2, and an upper end part facing the lower end part 2. The upper end part is provided with a cap neck 3 which is in an annular shape and has a diameter smaller than that of the lower end part 2. The body 1 in an octagonal prism shape is formed of eight planar surfaces in which two opposed surfaces are substantially parallel to each other. Since the bottle 10 also serves as a tube for centrifugation, the closed lower end part 2 is in a conical or octagonal conical shape. The body 1 corresponds to the container body. The cell culture container is an example of the liquid container of the present embodiment.

The cap neck 3 has an upper end face serving as an opening portion 4. The cap neck 3 has an outer periphery formed with a thread 6 to which a cap 5 having a threaded inner periphery is mounted. In other words, the cap 5 is a screw cap. To facilitate mechanically controlled rotary cultivation, the bottle 10 is provided with a ridge 7. The ridge 7 is formed on the outer periphery of the bottle 10. So as to be located at a joint between the cap neck 3 and the body 1. The ridge 7 is used for fixing a grip member or a punched member thereto when the octagonal prism body 1 is held vertically or horizontally, or the culture medium accommodated in the body 1 is decanted, with the opening portion 4 oriented obliquely downward.

Figure 1B:
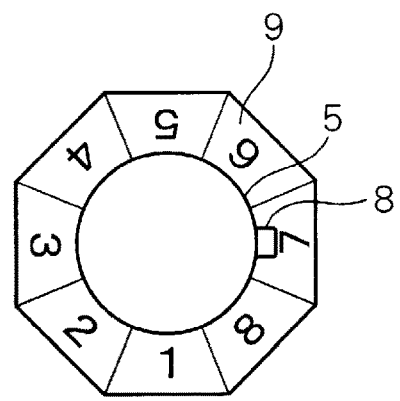
Figure 2:
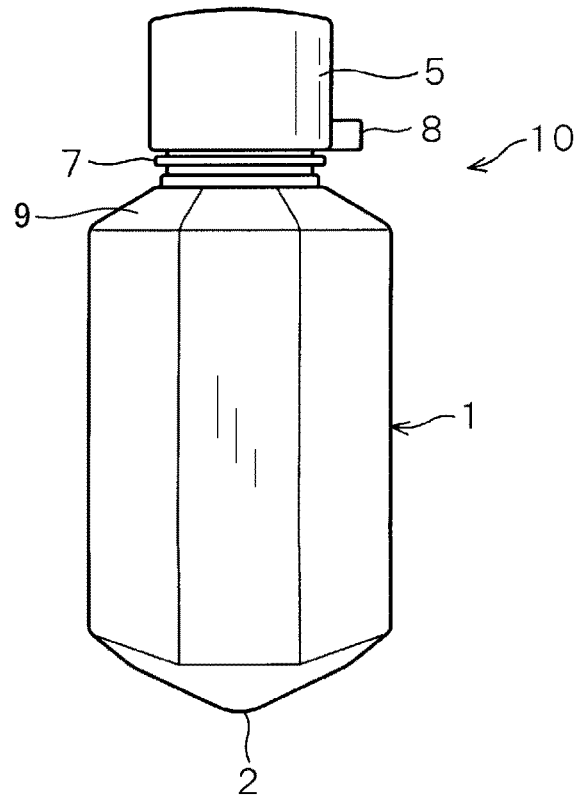
FIG. 2 is a front view of the bottle.
Figure 3:
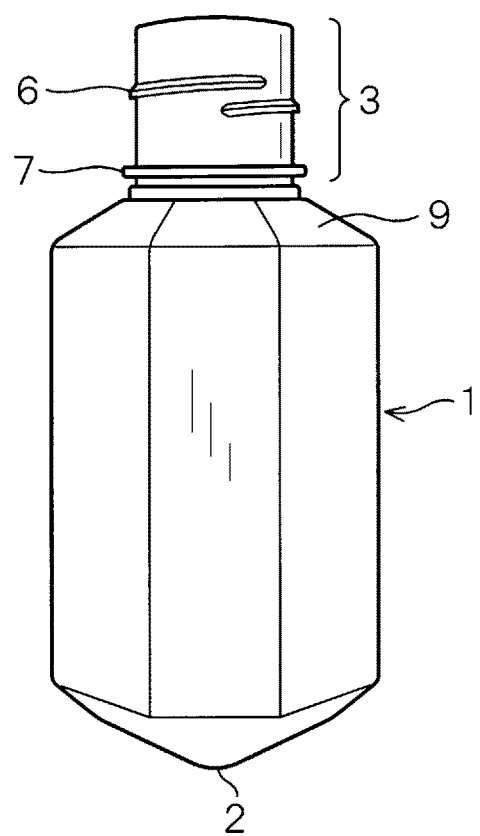
FIG. 3 is a front view of the bottle with the cap detached.
Figure 4:
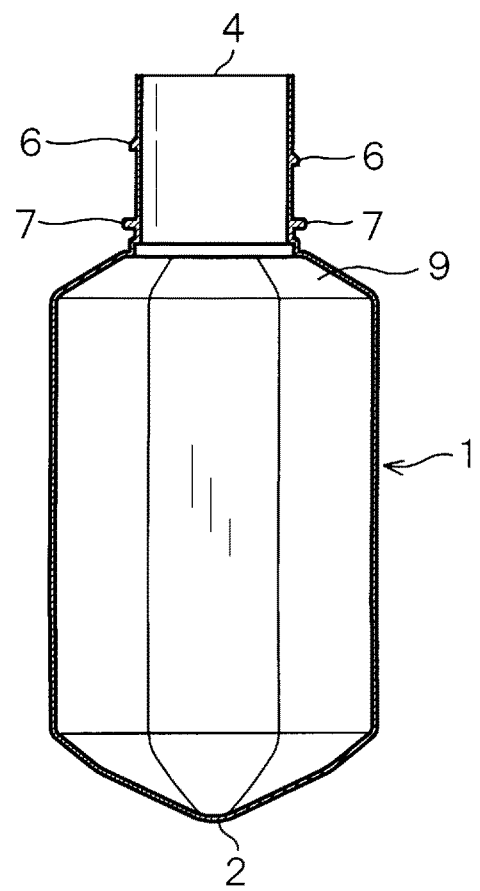
FIG. 4 is a longitudinal cross-sectional front view of the bottle with the cap detached.

As shown in FIGS. 1A, 1B and 2, the cap 5 has an outer periphery which is formed with a protrusion 8 having a length of 1 mm or more, for example on a lower end thereof (see FIG. 2). As will be described later, the protrusion 8 is used when the robot hand rotates the cap 5 to perform an opening or closing task. The cap neck 3 has a lower peripheral end from which an upper surface of the bottle 10 extends to the upper peripheral end of the octagonal prism body 1 formed of eight planar surfaces. The upper surface that surrounds the cap neck 3 is designated with numerals 1 to 8 corresponding to the respective eight planar surfaces of the octagonal prism body 1. These numerals serve as a position indicator 9. As will be described later, the position indicator 9 is used for control of the robot. The protrusion 8 corresponds to the torque receiver as a constituent of the mark, while the position indicator 9 corresponds to the reference mark as a constituent of the mark.

Materials that can be used for forming the bottle 10 include, but are not limited to, materials generally used for cell culture. Examples of generally used materials include resin materials, inorganic materials, such as glass and quartz, metals and the like. From the viewpoint of ease of manufacture, cost reduction, or ease of keeping track of cell culture conditions, resin materials are preferably used. Accordingly, considering ease of manufacture, cost reduction, or ease of keeping track of cell culture conditions, the material used for forming the bottle 10 is preferably selected from the group consisting of polyethylene terephthalate, polystyrene, polypropylene, polyethylene, polytetrafluoroethylene, polyvinyl chloride, and mixtures of these materials.

Figure 11:
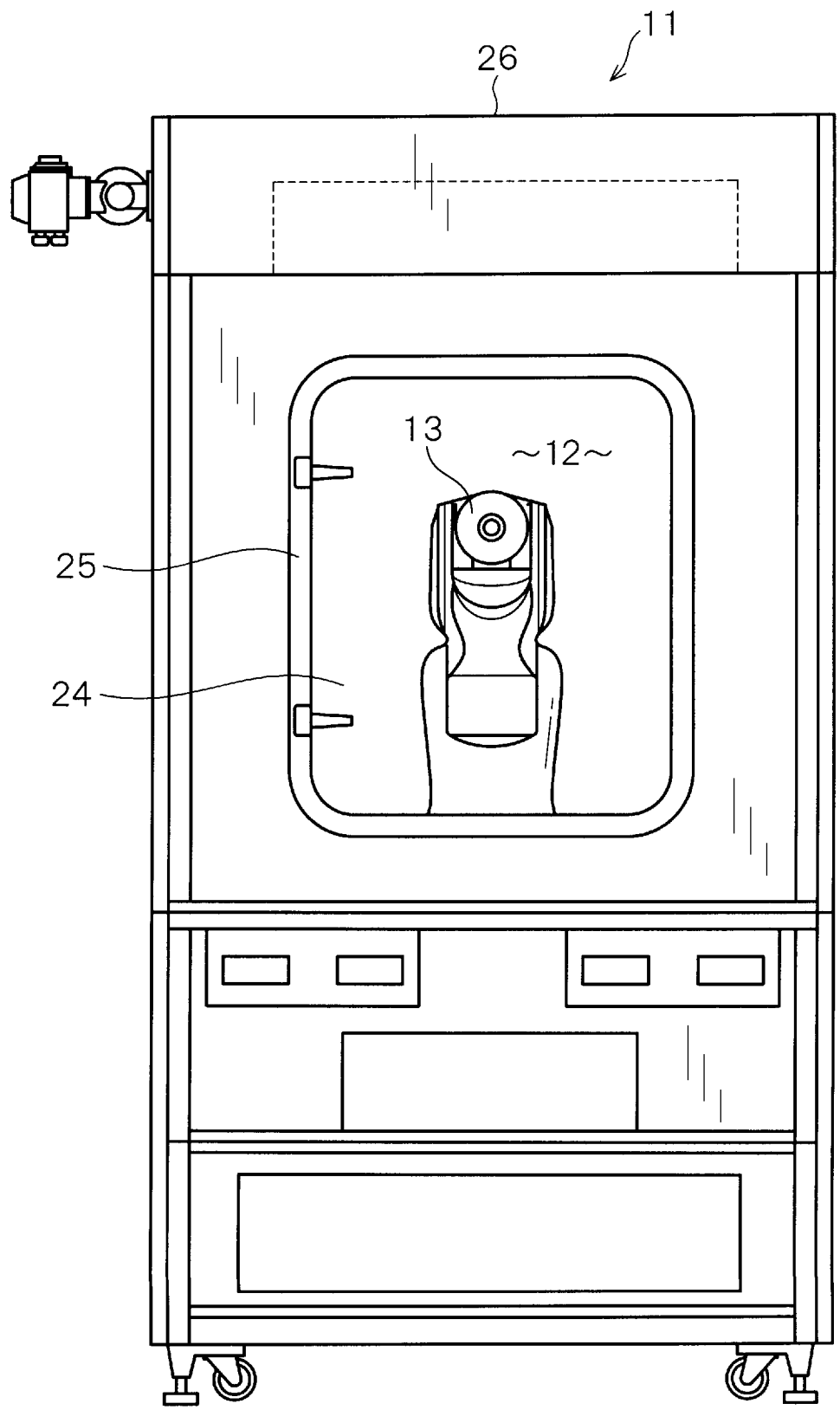
FIG. 11 is a front view of an automatic cell culture apparatus.
Figure 12:
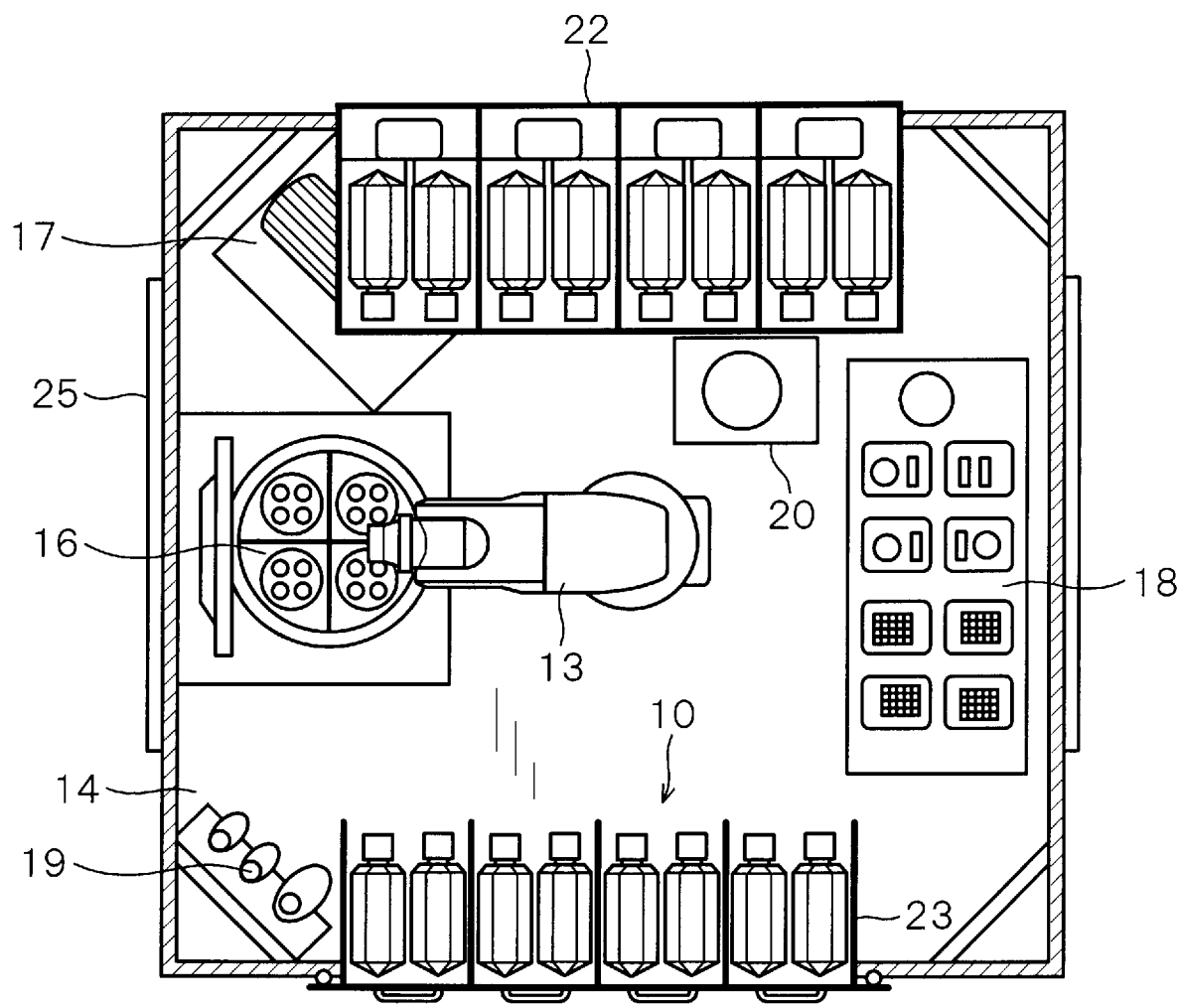
FIG. 12 is a plan view of the interior of a working chamber of the automatic cell culture apparatus.
Figure 13:
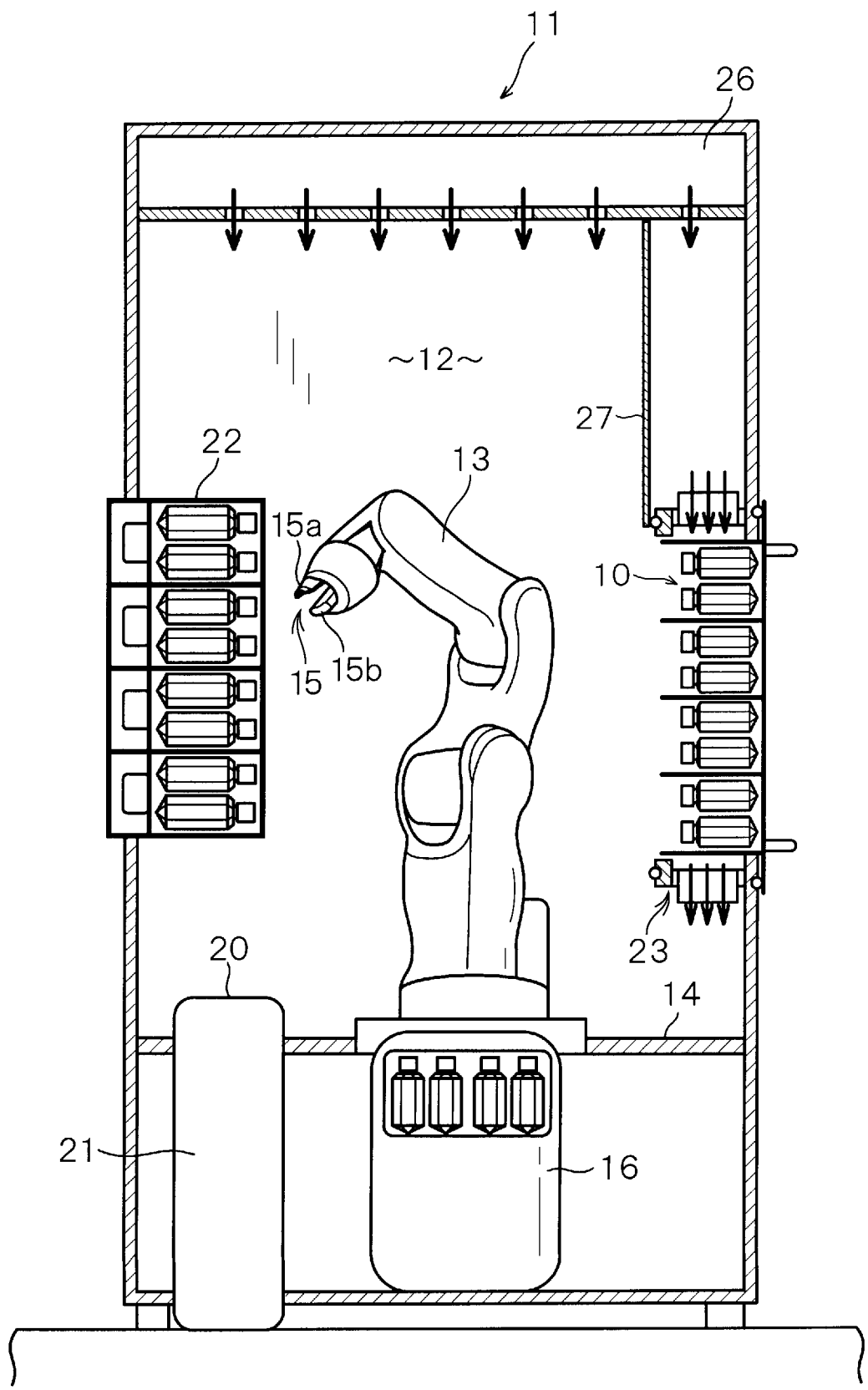
FIG. 13 is a cutaway front view of the interior of the working chamber.

FIG. 11 is a front view of an automatic cell culture apparatus 11. The automatic cell culture apparatus 11 includes a working chamber 12 at the center of which a robot arm 13 is arranged. FIGS. 12 and 13 are plan view and front view, respectively, of the working chamber 12. As shown in these figures, the robot arm 13 is rotatably set up on a floor board 14 of the working chamber 12. The robot arm 13 includes a hand 15 which is rendered to be rotatable by three joint mechanisms and to be rotatable in a twisting direction around an axis of each joint mechanism. In other words, the robot arm 13 has a 6-axis vertical configuration with 3 degrees of freedom for translation and 3 degrees of freedom for rotation. Thus, the hand 15 can be brought to any position and can adopt any posture in a predetermined movable range. The hand 15 is configured to grasp a work object with two claws 15a, 15b. The robot arm 13 is surface-treated in advance so as to have sterilization resistance and sanitary property.

As shown in FIG. 12 illustrating the interior of the working chamber 12, various peripheral devices and tools of the robot arm 13 are arranged on the floor board 14, such as a centrifugal separator 16, a microscope 17, a workbench 18 on which reagents or materials to be consumed are placed, pipetters 19, a disposal shutter 20 and the like. As shown in FIG. 13, the disposal shutter 20 opens/closes the opening portion of a disposal box 21 which is arranged beneath the floor board 14 to discard waste materials and waste liquid and the like. The working chamber 12 includes a peripheral wall on which an incubator 22, a pass box 23 and the like are arranged.

The working chamber 12 configures an enclosed space for performing medical tasks, such as cell culture. As shown in FIG. 11, the working chamber 12 has a front part to which an opening/closing door 25 is attached. The opening/closing door 25 includes a transparent monitoring window 25 for externally monitoring the tasks performed by the robot arm 13. As shown in FIGS. 11 and 13, the working chamber 12 has an upper part where a high efficiency particulate air filter (HEPA) unit 26 is arranged to sterilize the working chamber 12, and also to supply sterile outside air into the working chamber 12.

The pass box 23 accommodates several bottles 10. The pass box 23 has a front side which confronts the working chamber 12 and is covered/uncovered in the front side by a shutter 27 that is driven by an actuator, not shown. When the shutter 27 is opened, the robot arm 13 extracts a bottle 10 arranged in the pass box 23 using the hand 15.

As shown in FIGS. 5A to 5C and FIGS. 6A and 6B, the claws 15a, 15b configuring the hand 15 each have a tip end in which a recess 28 is formed. The recess 28 is provided to establish an engagement with the protrusion 8 of the cap 5 when the hand 15 grasps the cap 5 in the motion of taking out a bottle 10 arranged in the pass box 23, or in the motion of opening or closing the bottle 10.

Figure 7:
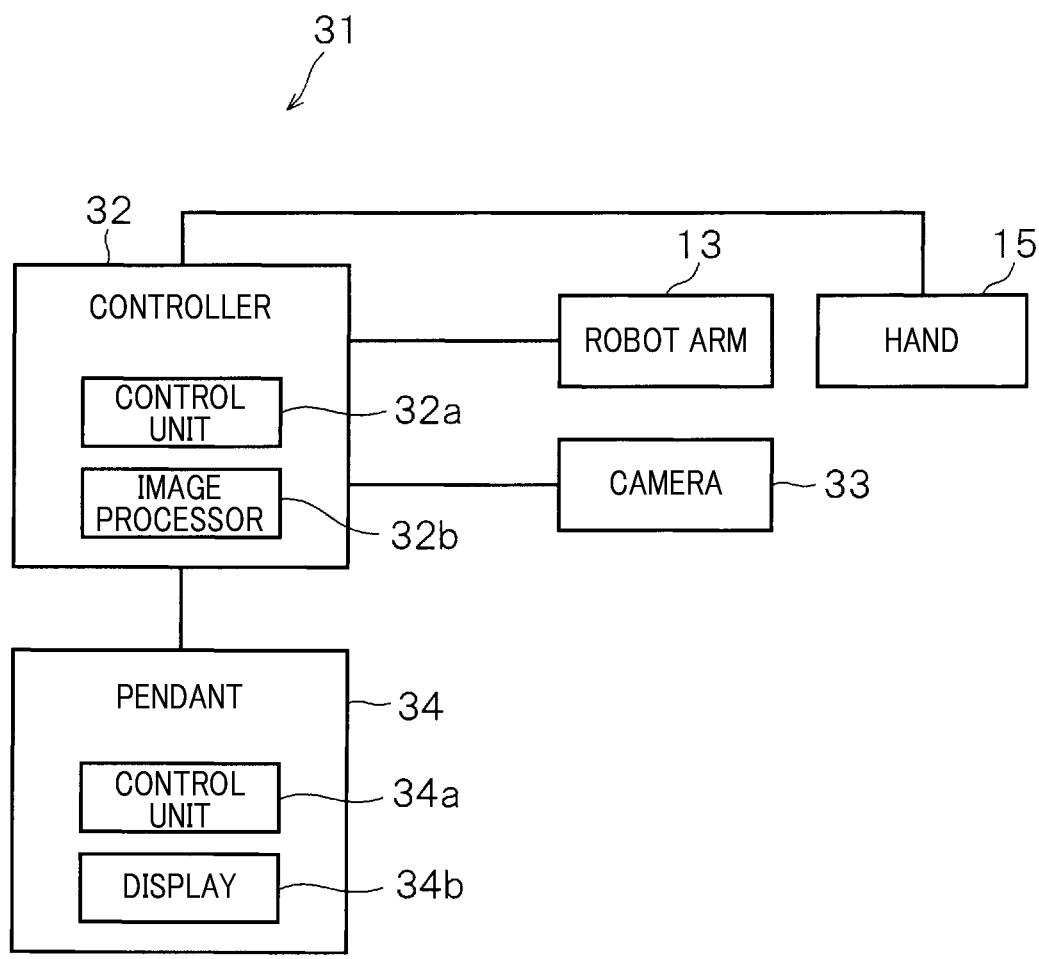
FIG. 7 is a functional block diagram illustrating an overall configuration of a robot system, according to the present invention.

FIG. 7 is a functional block diagram illustrating an overall configuration of a robot system 31 including a controller 32, a camera 33, and a pendant 34. In the robot system 31, the controller 32 includes a control unit 32a configured by a microcomputer, and an image processor 32b. The image processor 32b processes an image captured by the camera 33 which is arranged at the hand 15 to thereby determine a reference position for the task. The controller 32 corresponds to the control apparatus.

The camera 33 corresponding to the imager is connected to the controller 32 and captures an image of the work or the like, i.e. a work object, located ahead of the hand 15. The data of the image captured by the camera 33 is transmitted to the controller 32, and image-processed by the image processor 23b to determine the position of the work.

The pendant 34 includes a control unit 34a and a display 34b, and is connected to the controller 32 via a connecting cable. The pendant 34, which is also referred to as a teaching pendant, is used, for example, for determining the trajectory or various parameters of the robot arm 13. By manually operating the pendant 34, the posture of the robot arm 13 can be controlled. The display 34b includes a touch panel, not shown, for the input of the user's touch operation.

Figure 5A:
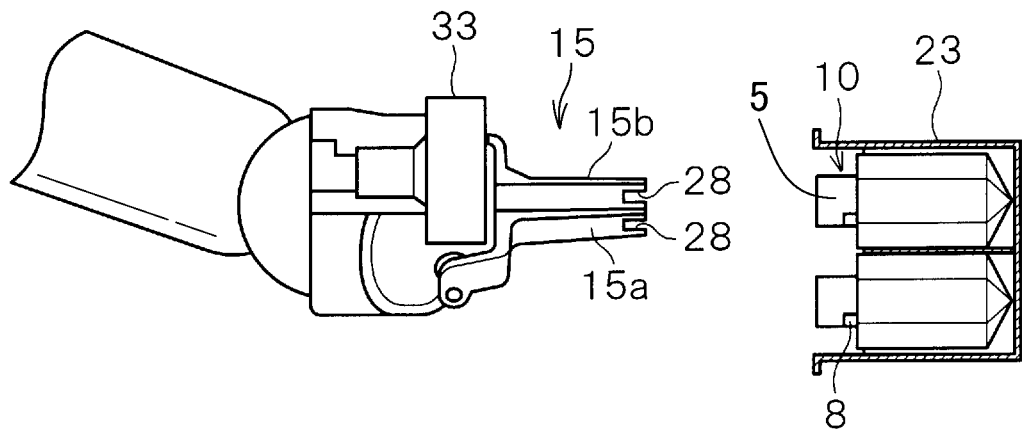
FIGS. 5A to 5C are diagrams illustrating a motion of a robot hand when taking out the bottle from a pass box.
Figure 5B:
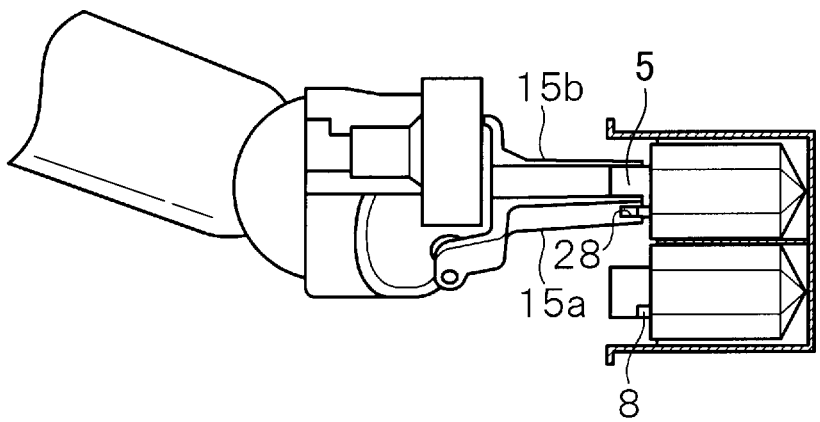
Figure 5C:
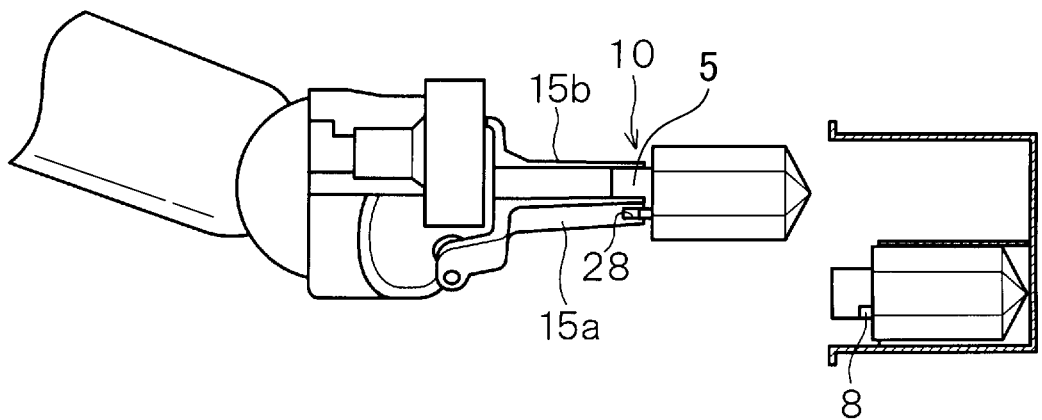
Figure 8:
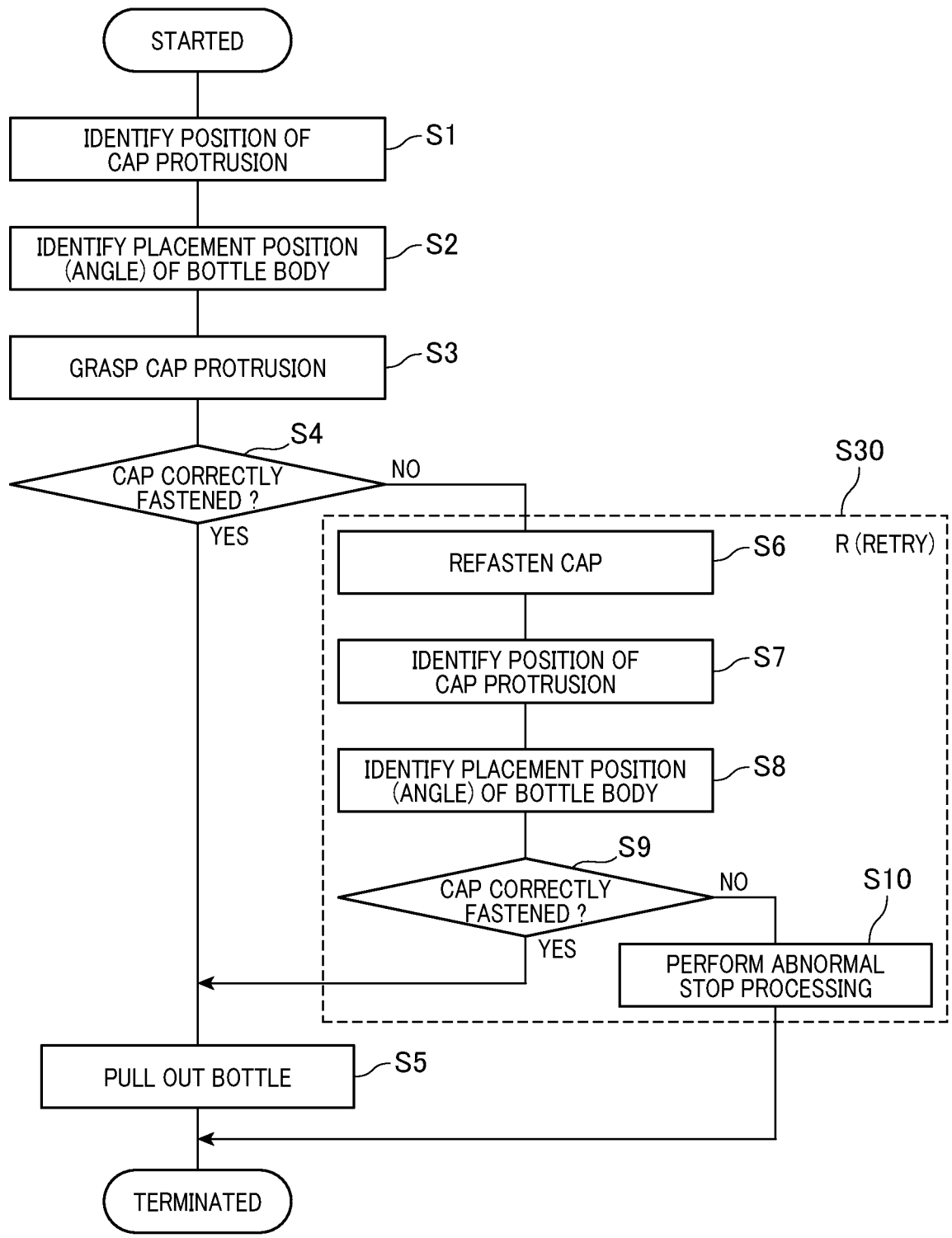
FIG. 8 is a flow diagram illustrating the processing corresponding to the motion illustrated in FIGS. 5A to 5C.

The following description addresses the operation of the present embodiment. FIGS. 5A to 5C show a motion of the robot hand 15 when taking out a bottle 10 from the pass box 23. FIG. 8 is a flow diagram corresponding to the motion shown in FIGS. 5A to 5C. The bottle 10 is accommodated in the bass box 23, with part of the planar surfaces of the octagonal prism body 1 being contacted with part of the inner walls of the pass box 23. Specifically, the body 1 is fixed to the pass box 23 in the accommodated state.

In the state shown in FIG. 5A, the camera 33 located at the hand 15 captures, from the cap 5 side, an image of the bottle 10 accommodated in the pass box 23. The controller 32 identifies the position of the protrusion 8 of the cap 5 from the image data derived from the camera 33 (step S1), and then identifies the placement position and the angle of the body 1, based on the identified position of the protrusion 8 (step S2).

Figure 6A:
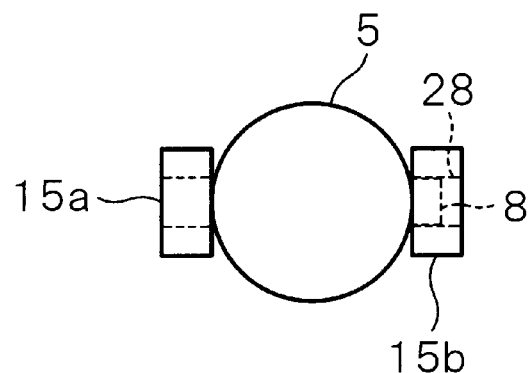
FIGS. 6A and 6B are front view and side view, respectively, of the robot hand, with its claws grasping the cap.
Figure 6B:
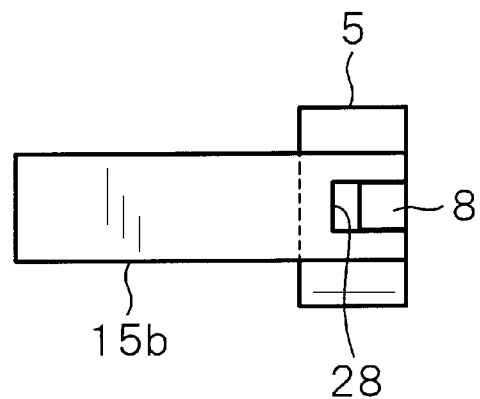

Then, the controller 32 causes the hand 15 to move rightward, as viewed in the figure, with the claws 15a, 15b open, and permits the tip ends of the claws 15a, 15b to enter the pass box 23. Then, as shown in FIG. 5B, the controller 32 causes the claws 15a, 15b to close so that the cap 5 is grasped, with the protrusion 8 being engaged with one of the recesses 28 (step S3). FIGS. 6A and 6B are schematic front and side views, respectively, showing the state in which the recess 28 is engaged with the protrusion 8.

Subsequently, the controller 32 determines whether the cap 5 is correctly fastened to the body 1, i.e., whether the bottle 10 is correctly closed (step S4). It should be noted that, as a precondition, the projection 8 is brought to an initial position, for example, the position 1 of the position indicator prior to starting the task of fastening the cap 5 to the body 1. Also, as a precondition, the cap 5 is rotated by a predetermined amount from the initial position, and the resultant position where the protrusion 8 is located after completing fastening, with a predetermined torque being applied, i.e. a fastening completion position, is, for example, the position 7 of the position indicator 9. Details of this task will be described later.

Accordingly, the controller 32 determines, at step S4, that the cap 5 is correctly fastened to the body 1 if the protrusion 8 is positioned at the fastening completion position, i.e. the position 7, of the position indicator 9 (YES at step S4). In this case, as shown in FIG. 5C, the hand 15 is caused to directly move leftward, as viewed in the figure, to pull out the bottle 10 from the pass box 23 (step S5), and then the processing is terminated.

If the protrusion 8 is not positioned at the position 7 of the position indicator 9, but instead is positioned at the position 6, for example, it is determined, at step S4, that the cap 5 is loose and is not at the correctly closed position, i.e. is not correctly fastened (NO at step S4). In this case, to refasten the cap 5, the controller 32 causes the hand 15 to rotate in the closing direction, with the cap 5 being grasped by the claws 15a, 15b (step S6). Then, at the subsequent steps S7 and S8, processing similar to steps S1 and S2 are performed, and, at step S9, determination processing similar to step S4 is performed. If the cap 5 is determined to be correctly fastened (YES at step S9), control proceeds to step S5, but if determined not to be correctly fastened (NO at step S9), abnormal stop processing is performed (step S10).

Figure 9:
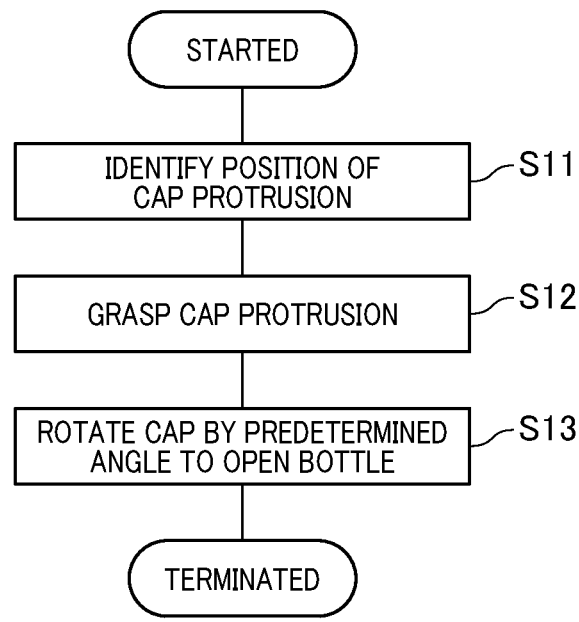
FIG. 9 is a flow diagram illustrating the processing for opening the bottle performed by the robot hand.

FIG. 9 is a flow diagram of the processing for opening the robot hand 15 performed by the bottle 10. The opening task is performed, for example, by bringing the bottle 10 extracted from the pass box 23 to the workbench 18, and fixing the body 1. Similarly to step S1, the controller 32 identifies the position of the protrusion 8 of the cap 5 (step S11). Then, similarly to the motion shown in FIGS. 5A to 5C, the hand 15 is brought close to the cap 5, with the claws 15a, 15b open.

Then, the claws 15a, 15b are closed to grasp the cap 5, with one of the recesses 28 brought into engagement with the protrusion 8 (step S12). The grip force imparted to the cap 5 by closing the claws 15a, 15b during the opening task may be substantially zero. Then, on the precondition that the protrusion 8 is at the fastening completion position mentioned above, the controller 32 causes the grasped cap 5 to rotate by a predetermined amount in the opening direction to open the bottle 10 and detach the cap 5 (step S13).

Figure 19:
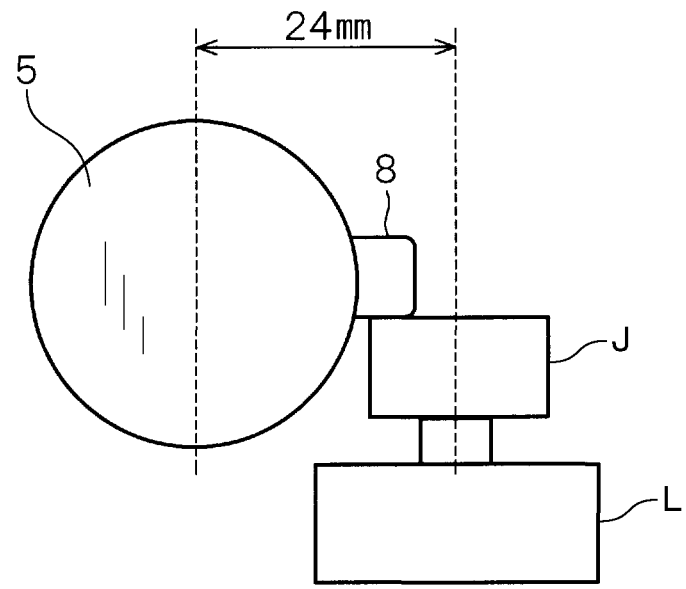
FIG. 19 schematically illustrates measurement of torque which is applied to the cap when a bottle is opened.

When performing the opening task as described above, the torque imparted to the cap 5 by the hand 15 may be in the range of not less than 0.7 Nm to not more than 1.5 Nm. FIG. 19 is a schematic diagram illustrating a state where the torque required for opening the correctly closed cap 5 is measured. The bottle 10 is laid down, and a measuring jig J is interposed between a load meter L set up on a desk or the like and the protrusion 8. In this state, the body 1 is rotated in the opening direction so that the load meter can measure the torque required for the opening. The load changes in a range of 30N to 60N, depending on the tightening force imposed to the cap 5 during the closure. In this case, the torque required for opening the bottle 10 is in the range of 0.7 Nm to 1.5 Nm.

Figure 10:
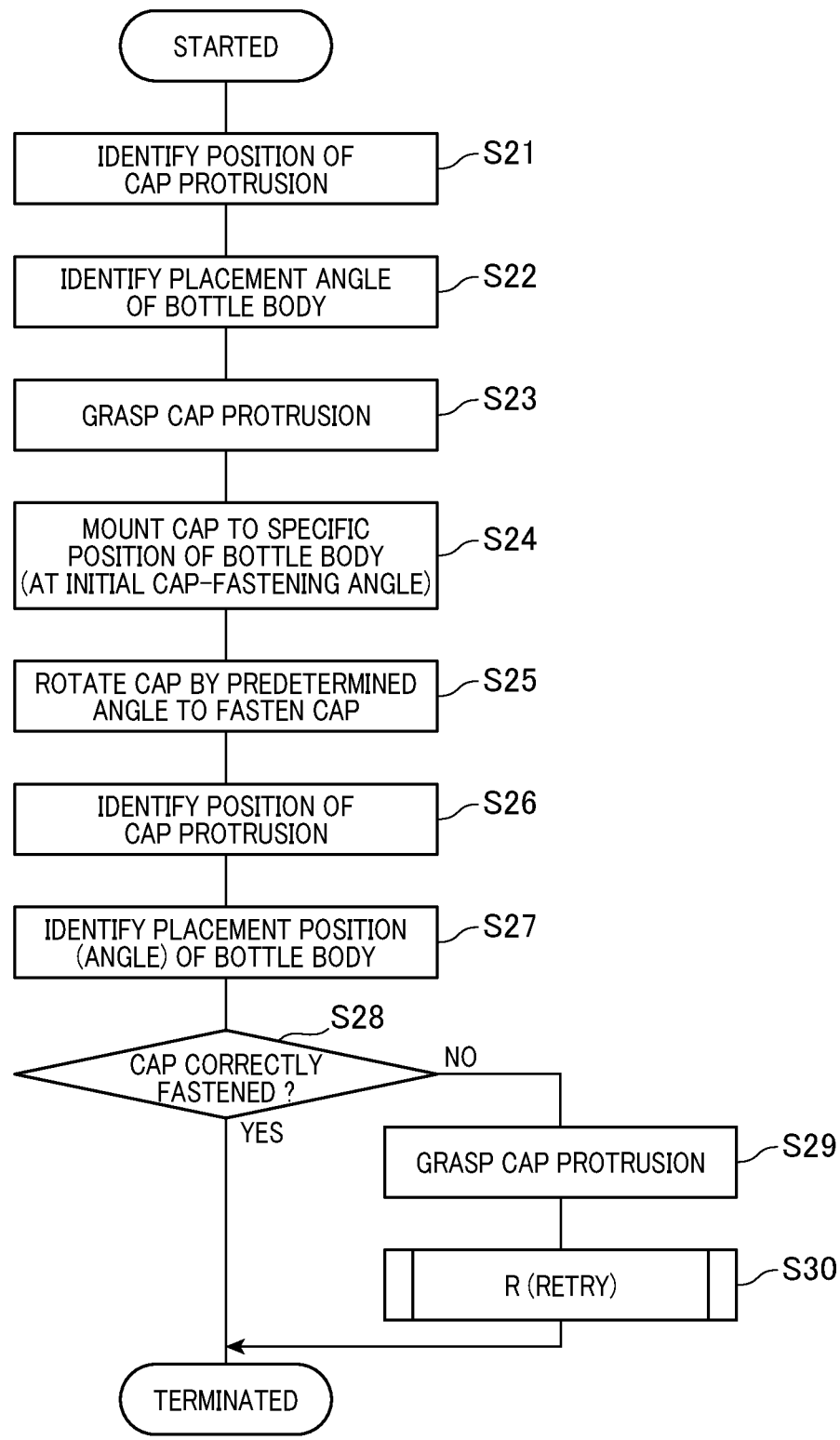
FIG. 10 is a flow diagram illustrating the processing for closing the bottle performed by the robot hand.

FIG. 10 is a flow diagram illustrating the processing for closing the bottle 10 performed by the hand 15. Steps S21 to S23 are performed similarly to steps S1 to S3, respectively, although the bottle 10 is in the state where the cap 5 is detached from the body 1. Accordingly, at step S23, the controller 32 causes the hand 15 to grasp the cap 5 and bring it close to the cap neck 3 of the body 1. Then, the protrusion 8 is ensured to be positioned at a specific position of the body 1, i.e., at the position 1 of the position indicator 9 that is the initial position as mentioned above, to thereby mount the cap 5 to the cap neck 3 of the body 1 (step S24). Then, the cap is rotated by a predetermined angle in the direction of fastening the cap 5, i.e. in the closing direction (step S25).

Then, similarly to steps S1 and S2, the controller 32 identifies the position of the protrusion 8 and the placement angle of the body 1, followed by determining, similar to step S4, whether the cap 5 is correctly fastened (step S28). If it is determined that the cap 5 is correctly fastened (YES at S28), the processing is terminated. If it is determined that the cap 5 is not correctly fastened (NO at S28), the cap 5 is grasped by the claws 15a, 15b (step S29), and refastening of the cap 5, i.e. a retry, is performed (step S30). The retry at step S30 corresponds to steps 6 to S10 shown in FIG. 8.

After refastening the cap 5, the bottle 10 in question may be discarded into the disposal box 21. Specifically, if the bottle 10 is not properly closed, the accommodated material or the like may have been contaminated. Therefore, the bottle 10 may be discarded after being completely closed so that the accommodated material or the like does not leak out, thereby preventing contamination inside the working chamber 12.

As described above, according to the present embodiment, the bottle 10 includes the body 1 and the cap 5 mounted to the cap neck 3 of the body 1, and the cap 5 has an outer peripheral portion provided with the protrusion 8. Further, the cap neck 3 has a peripheral portion provided with the position indicator 9 which indicates whether the cap 5 is at a correctly closed position, based on the positional relationship between the protrusion 8 and the position indicator 9. Further, the robot hand 15 includes the camera 33 for capturing an image of the two claws 15a, 15b, and the position indicator 9 of the body 1 for identification purposes, while the claws 15a, 15b are formed with respective recesses 28.

With this configuration, the robot-side controller 32 can obtain information on the positional relationship between the protrusion 8 of the cap 5 and the position indicator 9 prior to starting an opening task, from the image captured by the camera 33 which is arranged at the robot hand 15, to thereby determine whether the cap 5 is at a correctly closed position.

Also, the robot-side controller 32 can visually obtain information on the amount of rotation of the cap 5 from the initial closed position, from the image showing the positional relationship between the protrusion 8 and the position indicator 9. Accordingly, the information on the amount of rotation of the cap 5 required for opening the bottle is obtained at the same time, so that the task of opening the bottle 10 is facilitated. In this regard, the position indicator 9 contributes to more easily and specifically obtaining information on the positional relationship between the cap 5 and the body 1. This owes to the fact that the position indicator 9 has a configuration in which the area around the cap neck 3 is circumferentially evenly divided into a plurality of small areas discriminated from each other, with serial numbers being designated to and indicated in the respective small areas.

In the position indicator 9 of the present embodiment, numerals 1 to 8 are designated to the respective small areas around the cap neck 3. Accordingly, when the cap 5 is refastened at step S6 or S30, information on the amount of rotation of the cap 5 required for correctly fastening the cap 5 is easily obtained. When refastening the cap 5, excessive rotation of the cap 5 may cause friction between the cap 5 and the claws 15*a*, 15*b* of the robot hand 15, and thus may produce wear debris. In this regard, the present embodiment can easily obtain information on the amount of rotation of the cap 5 when refastened, and thus production of wear debris is reliably prevented.

Further, the cap 5 is easily rotated with one of the recesses 28 of the claws 15*a*, 15*b* brought into engagement with the protrusion 8, to thereby prevent occurrence of friction between the cap 5 and the claws 15*a*, 15*b*. In addition, provision of the protrusion 8 to the cap 5 can render the grip force to be substantially zero, which is applied to the cap 5 when the claws 15*a*, 15*b* are closed to perform the opening task. Accordingly, the cap 5 is prevented from being abraded by the claws 15*a*, 15*b* having high rigidity, to thereby reliably prevent production of wear debris.

Further, provision of the recesses 28 to the respective claws 15*a*, 15*b* enables easier engagement with the protrusion 8. In addition, since the robot hand 15 has only two claws 15*a*, 15*b*, only a minimum number of openings is required to be provided for establishing communication between the exterior and the interior that includes the actuators for driving the claws, leading to easy sealing of the openings. Accordingly, when applied to the tasks performed inside the sterilized working chamber 12, the robot hand 15 has a structure adapted for improving cleaning properties.

In the robot system 31 of the present embodiment, the controller 32 acquires image data of the cap 5 and the position indicator 9 of the bottle 10 from the camera 33 provided to the hand 15, to thereby determine whether the cap 5 is at the correctly closed position, based on the positional relationship between the protrusion 8 of the cap 5 and the position indicator 9. Accordingly, non-contamination of the material or the like in the bottle 10 can be confirmed prior to performing the task of opening the bottle 10.

If the cap 5 is determined to be at the correctly closed position, the controller 32 causes the robot hand 15 to grasp the cap 5, for rotation by a predetermined angle in the opening direction, thereby performing the task of opening the bottle 10. Thus, the opening task can be reliably performed, while the positional relationship between the protrusion 8 and the position indicator 9 is confirmed based on the image data.

Furthermore, if the cap 5 is determined not to be at the correctly closed position, the controller 32 causes the robot hand 15 to grasp the cap 5, for rotation by a predetermined angle in the closing direction, to thereby perform the task of closing the bottle 10. Then, the closed bottle 10 is discarded. Thus, leakage of the material or the like accommodated in the bottle 10 is prevented, and contamination on the inside of the working chamber 12 is prevented.

Second and Third Embodiments

Figure 14:
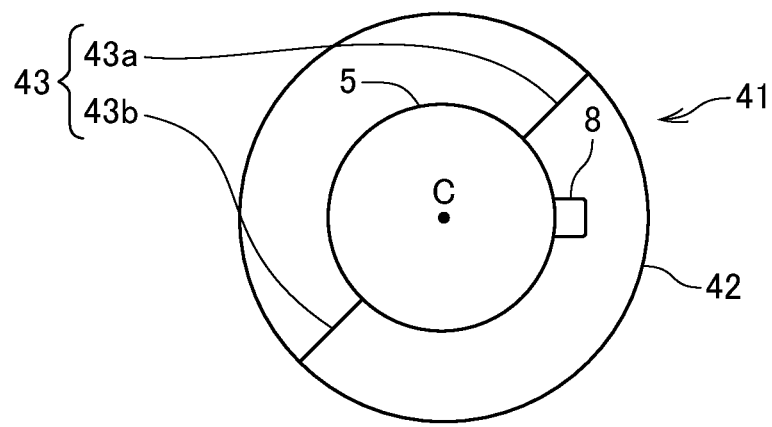
FIG. 14 is a plan view of a bottle with the cap attached, according to a second embodiment of the present invention.
Figure 15:
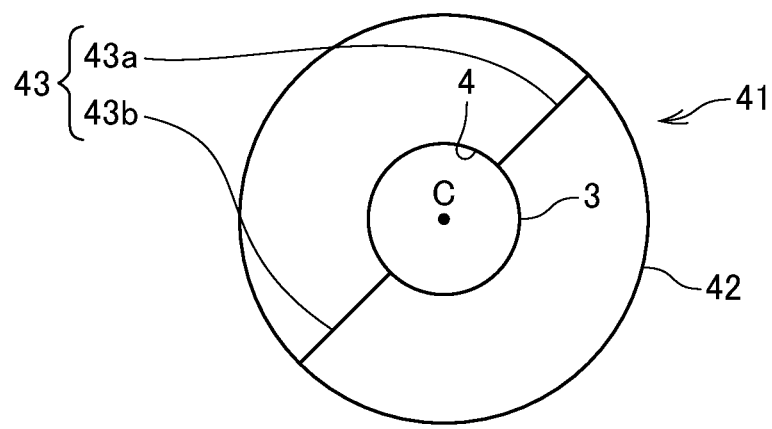
FIG. 15 is a plan view of the bottle with the cap detached.

In the following description, the components identical with or similar to those of the first embodiment are given the same reference numerals for the sake of omitting duplicate description. The following description is focused on the differences from the first embodiment. The second and third embodiments exemplify variations of the position indicator provided to the bottle body. FIGS. 14 and 15 show a bottle 41 according to the second embodiment. The bottle 41 includes a prism body 42 having a position indicator 43. The position indicator 43 is configured to two line segments which are part of a straight line passing through a center C of the body 42. Specifically, the position indicator 43 is configured to a line segment 43*a* which is defined between the outer periphery of the cap neck 3 and the outer periphery of the body 42, and another line segment 43*b* which is defined similarly to the line segment 43*a*.

In the second embodiment, the following process is taken when determining whether the cap 5 is correctly fastened to the body 1, i.e. when determining, at step S4 (see FIG. 8), whether the bottle 41 is correctly closed.

As a precondition herein, the protrusion 8 is brought to an initial position of the position indicator 43 of the body 42, e.g., is aligned with the line segment 43*b* as the initial position, prior to starting the task of fastening the cap 5 to the body 42. Further, as a precondition, when the cap 5 is rotated by a predetermined amount from the initial position to complete fastening, with a predetermined torque being applied to the cap 5, the resultant position where the protrusion 8 is located is a fastening completion position that is in alignment, for example, with the line segment 43*a*.

Accordingly, the controller 32 determines, at step S4, that the cap 5 is correctly fastened to the body 43 if the protrusion 8 is in alignment with the line segment 43*a* of the position indicator 43, that is, at the fastening completion position (YES at step S4).

If the protrusion 8 is determined, at step S4, not to be in alignment with the line segment 43*a* of the position indicator 43, but is determined, instead, to be located at a midpoint between the line segments 43*a* and 43*b*, for example, the controller 32 determines that the cap 5 is loose and is not at the correctly closed position, i.e., is not correctly fastened (NO at step S4).

When determining whether the protrusion 8 is in alignment with the line segment 43*a* or 43*b*, image data of the protrusion 8 and the line segments 43*a* and 43*b* acquired from the camera 33 is processed to detect the positions of the protrusion 8 and the line segments 43*a* and 43*b* in the image captured by the camera 33. The controller 32 determines that the protrusion 8 is in alignment with the line segment 43*a* or 43*b* if the detected position of the protrusion 8 matches the position of the line segment 43*a* or 43*b*. In this case, the controller 32 may determine that the protrusion 8 is in alignment with the line segment 43*a* or 43*b* even when the position of the protrusion 8 does not precisely match the position of the line segment 43*a* or 43*b*. Specifically, the controller 32 may determine the alignment if the position of the protrusion 8 falls within a predetermined range centering on the line segment 43*a* or 43*b*.

Figure 16:
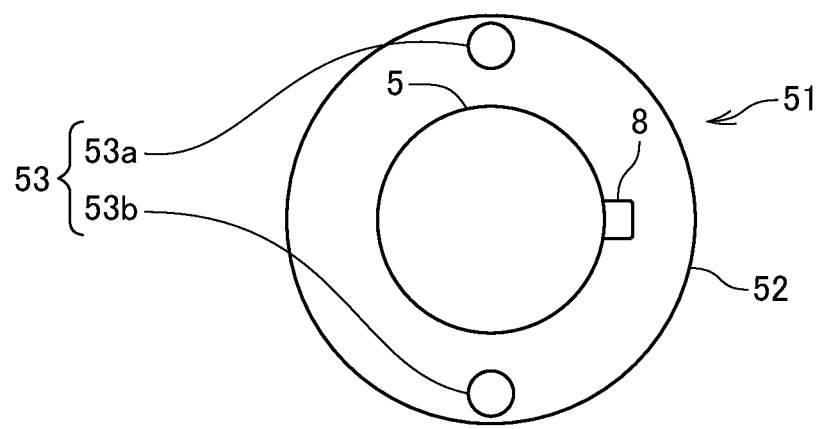
FIG. 16 is a plan view of a bottle with the cap attached, according to a third embodiment of the present invention.
Figure 17:
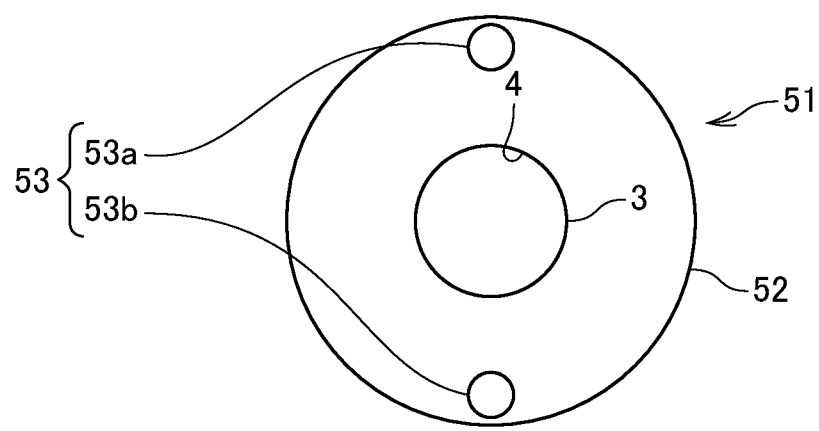
FIG. 17 is a plan view of the bottle with the cap detached.

FIGS. 16 and 17 show a bottle 51 according to the third embodiment. Similarly to the bottle 41, the bottle 51 is provided with a prism body 52 having a position indicator 53. The position indicator 53 is configured to circles 53*a*, 53*b* which are arranged on opposite sides of the bottle neck 3 so as to sandwich the bottle neck 3.

In the third embodiment, the following process is taken when determining whether the cap 5 is correctly fastened to the body 1, i.e. when determining, at step S4 (see FIG. 8), whether the bottle 51 is correctly closed.

As a precondition herein, the protrusion 8 is brought to an initial position of the position indicator 53 of the body 52, e.g., is aligned with the circle 53*b* as the initial position, prior to starting the task of fastening the cap 5 to the body 52. Further, as a precondition, when the cap 5 is rotated by a predetermined amount from the initial position to complete fastening, with a predetermined torque being applied to the cap 5, the resultant position where the protrusion 8 is located is a fastening completion position that is in alignment, for example, with the circle 53*a*.

Accordingly, the controller 32 determines, at step S4, that the cap 5 is correctly fastened to the body 53 if the protrusion 8 is in alignment with the circle 53*a* of the position indicator 53, that is, at the fastening completion position (YES at step S4).

If the protrusion 8 is determined, at step S4, not to be in alignment with the circle 53*a* of the position indicator 53, but determined, instead, to be located at a midpoint between the circles 53*a* and 53*b*, for example, the controller 32 determines that the cap 5 is loose and is not at the correctly closed position, i.e., is not correctly fastened (NO at step S4).

When determining whether the protrusion 8 is in alignment with the circle 53*a* or 53*b*, image data of the protrusion 8 and the circles 53*a* and 53*b* acquired from the camera 33 is processed to detect the positions of the protrusion 8 and the circles 53*a* and 53*b* in the image captured by the camera 33. The controller 32 determines that the protrusion 8 is in alignment with the circle 53*a* or 53*b* if the detected position of the protrusion 8 matches the position of the circle 53*a* or 53*b*. In this case, the controller 32 may determine that the protrusion 8 is in alignment with the circle 53*a* or 53*b* even when the position of the protrusion 8 does not precisely match the position of the circle 53*a* or 53*b*. Specifically, the controller 32 may determine the alignment if the position of the protrusion 8 falls within a predetermined range centering on the circle 53*a* or 53*b*.

As described above, the position indicators 43 and 53 of the second and third embodiments, respectively, can also provide information on the positional relationship between the position indicator 43 or 53 and the protrusion 8 of the cap 5.

Fourth Embodiment

Figure 18A:
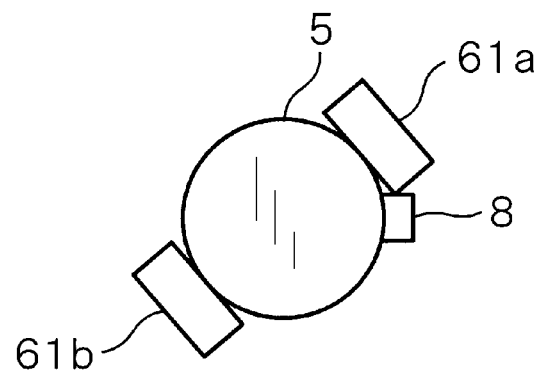
FIGS. 18A and 18B are front view and side view, respectively, of a robot hand with its claws grasping a cap, according to a fourth embodiment of the present invention.
Figure 18B:
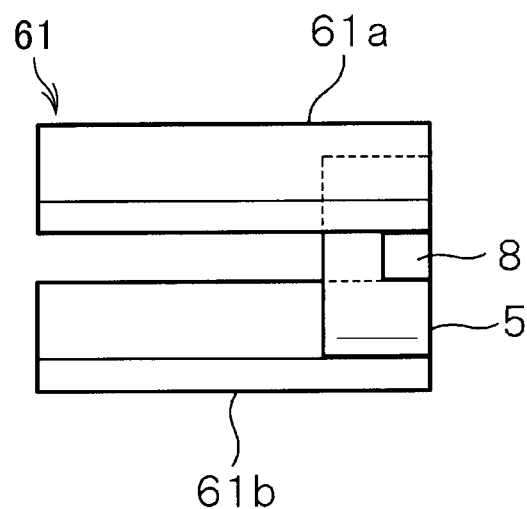

FIGS. 18A and 18B show a robot hand 61 of the fourth embodiment. As shown in these figures, the robot hand 61 is provided with two claws 61*a*, 61*b*, similarly to the robot hand 15 of the first embodiment. Unlike the first embodiment, however, these claws 61*a*, 61*b* are not provided with the recesses 28. The robot hand 61 with this shape can also grasp and rotate the cap 5, with part of a side portion of the claw 61*a*, for example, being abutted against the protrusion 8 of the cap 5, without causing friction therebetween.

The present invention should not be construed as being limited to the embodiments described above or illustrated in the drawings, but may be modified or extended as follows.

For example, in the first embodiment, the recess 28 may be provided to only one of the claws.

The length of the projection 8 may be changed as appropriate in conformity with individual design.

The number of claws of the robot hand may be three or more.

Figure 20:
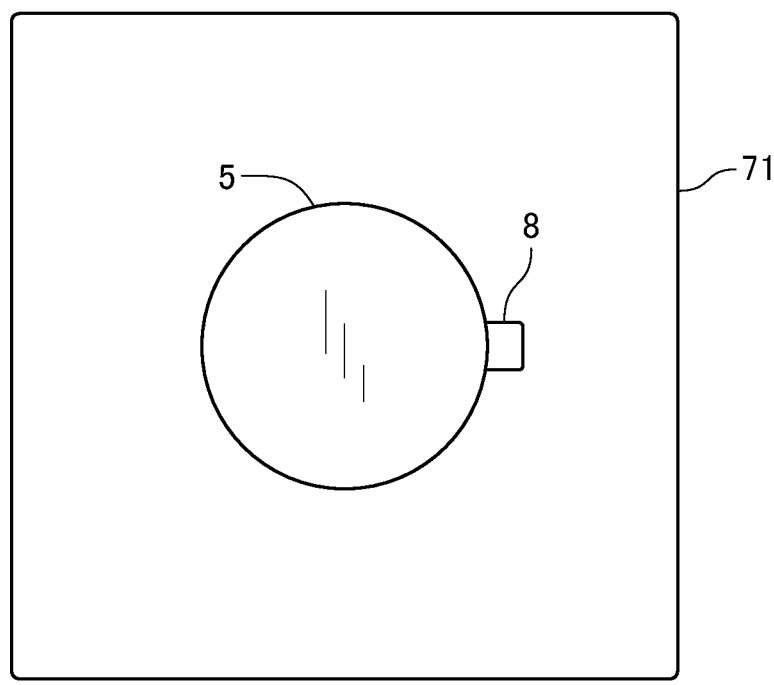
FIG. 20 illustrates a container with a modified shape.
Figure 21A:
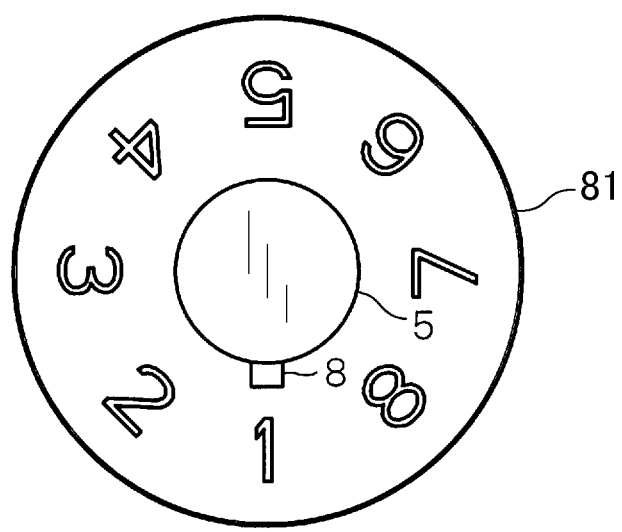
FIGS. 21A and 21B illustrate another container with a modified shape.
Figure 21B:
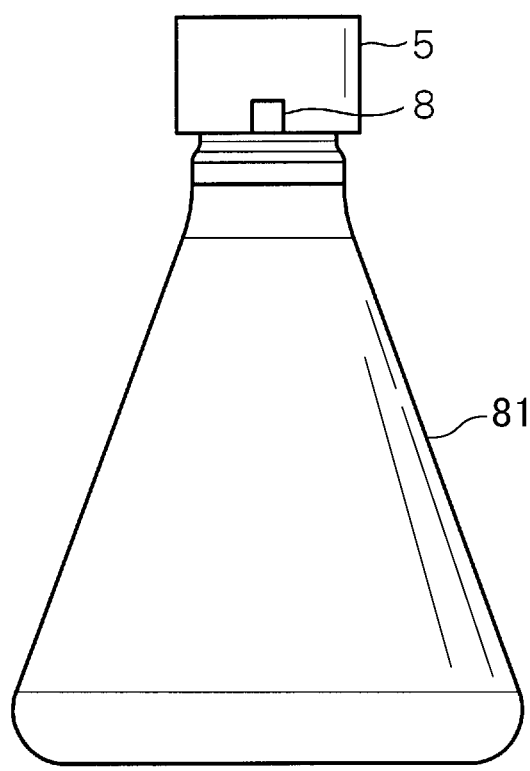
Figure 22A:
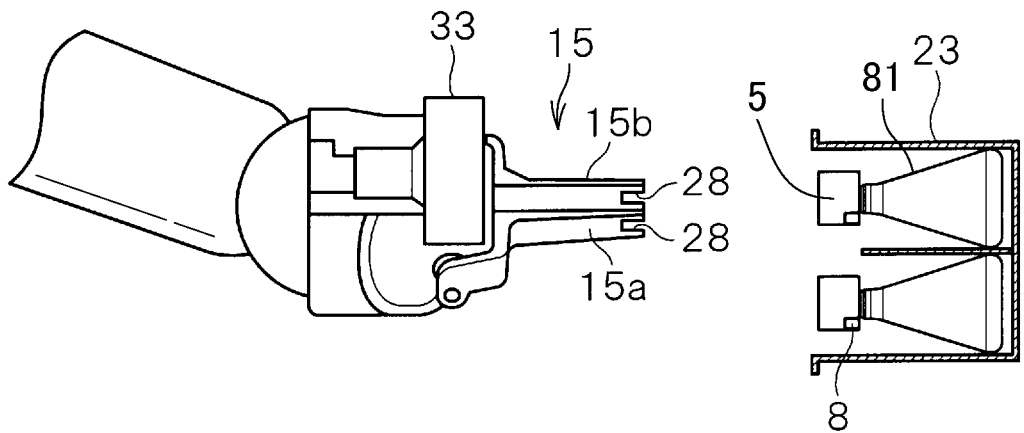
FIGS. 22A to 22C are diagrams corresponding to FIGS. 5A to 5C, respectively.
Figure 22B:
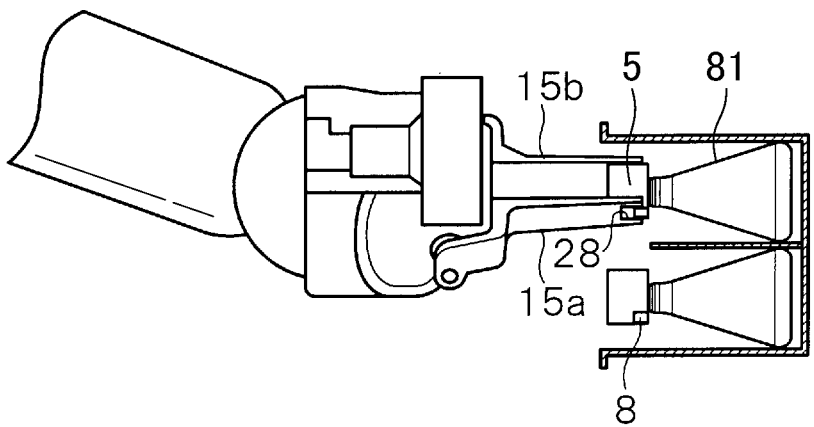
Figure 22C:
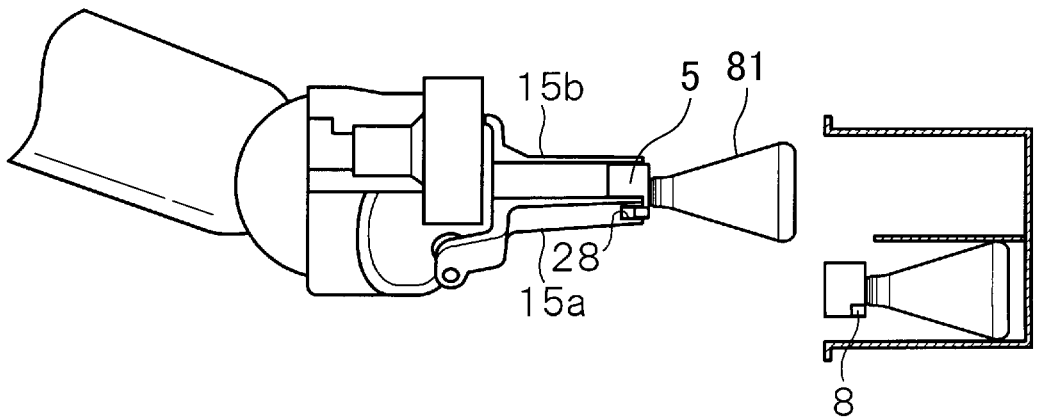

The bottle body is not limited to have an octagonal prism shape, but may have other polygonal prism shapes. For example, a bottle 71 having a quadratic prism shape as shown in FIG. 20, or a flask-shaped bottle 81 as shown in FIGS. 21A and 21B may serve as a bottle body. For example, the bottle having a flask-shaped body can be extracted from a pass box with a motion as shown in FIGS. 22A to 22C.

The interior of the working chamber does not have to be necessarily sterilized.

The liquid container of the present invention is not limited to a cell culture container. Any container may be handled by the robot hand as long as the container is assumed to be subjected to at least an opening task performed in a working chamber.

What is claimed is:

1. A robot system for performing an opening or closing task for a liquid container, the system comprising:
    a robot hand comprising:
        two or more claws for grasping the liquid container, the liquid container including a body provided with an opening portion and a cap mounted to the opening portion of the body, the liquid container being configured to be subjected to opening or closing of the cap performed by the robot hand, and the liquid container comprising:
            a protrusion formed to partially protrude outwards from an outer peripheral portion of the cap in a circumferential direction of the container, the protrusion being graspable by the two or more claws by engagement realized between the protrusion and a recess of the claws; and
            a position indicator provided to a peripheral portion of the opening portion and located below the protrusion in an extending direction of the body, the protrusion indicating whether the cap is at a correctly closed position of the cap based on a positional relationship between the protrusion and the position indicator obtained when viewing along the extending direction;
    an imager capturing an image of the liquid container in the extending direction; and
    a control apparatus (i) acquiring the image of the position indicator captured by the imager and (ii) identifying at least the correctly closed position of the cap based on the positional relationship between the protrusion and the position indicator obtained by processing the captured image.

2. The robot system according to claim 1, wherein the recess is provided to a tip end of at least one of the two or more claws and formed to be recessed from the tip in the extending direction.

3. The robot system according to claim 1, wherein the two or more claws are two claws.

4. The robot hand according to claim 1, wherein the position indicator includes a plurality of small areas that are discriminated from each other, the small areas being obtained by dividing an area around the opening portion in the circumferential direction of the container.

5. The robot hand according to claim 1, wherein the protrusion has a tip end which is located at a position radially inside an outer periphery of the body, when viewed from above the cap in a closed state in the extending direction.

6. A robot system comprising:
    a robot arm having a robot hand for performing an opening or closing task for a liquid container, the robot hand comprising:
        two or more claws for grasping the liquid container, the liquid container including a body provided with an opening portion and a cap mounted to the opening portion of the body, the liquid container being configured to be subjected to the opening or closing task of the cap performed by the robot hand, and the liquid container comprising:
- a protrusion formed to partially protrude outwards from an outer peripheral portion of the cap in a circumferential direction of the container, the protrusion being graspable by the two or more claws by engagement realized between the protrusion and a recess of the claws; and
- a position indicator provided to a peripheral portion of the opening portion and located below the protrusion in an extending direction of the body, the protrusion indicating whether the cap is at a correctly closed position of the cap based on a positional relationship between the protrusion and the position indicator obtained when viewing along the extending direction;

an imager capturing an image of the liquid container in the extending direction; and a control apparatus controlling the robot arm and comprising a microcomputer that performs a process enabling the control apparatus to functionally provide a process of (i) acquiring data of the image captured by the imager, the image including the cap and the position indicator, and (ii) determining whether the cap is at the correctly closed position based on a positional relationship between the protrusion and the position indicator obtained by processing the captured image.

7. The robot system according to claim 6, wherein the control apparatus functionally provides a process of causing the robot hand to grasp and rotate the cap in an opening direction of the cap by a predetermined angle to perform the opening task when it is determined that the cap is at the correctly closed position.

8. The robot system according to claim 6, wherein the control apparatus functionally provides processes of (i) causing the robot hand to grasp and rotate the cap in a closing direction of the cap by a predetermined angle to perform the closing task when it is determined that the cap is not at the correctly closed position and (ii) causing the robot hand to discard the closed liquid container.

* * * * *